United States Patent [19]

Aust et al.

[11] Patent Number: 5,603,713

[45] Date of Patent: * Feb. 18, 1997

[54] ANTERIOR LUMBAR/CERVICAL BICORTICAL COMPRESSION PLATE

[76] Inventors: Gilbert M. Aust, 14 Asbury La., Huntsville, Ala. 35802; Timothy E. Taylor, 1859 Shellbrook Dr., Huntsville, Ala. 35806

[ * ] Notice: The term of this patent shall not extend beyond the expiration date of Pat. No. 5,180,381.

[21] Appl. No.: 315,190

[22] Filed: Sep. 29, 1994

Related U.S. Application Data

[63] Continuation of Ser. No. 987,140, Dec. 8, 1992, abandoned, which is a continuation-in-part of Ser. No. 765,014, Sep. 24, 1991, Pat. No. 5,180,381.

[51] Int. Cl.$^6$ .......................... A61B 17/56; A61B 17/58
[52] U.S. Cl. ................ 606/61; 606/69; 128/898
[58] Field of Search .................. 623/17; 606/60, 606/61, 69–71, 65; 128/898

[56] References Cited

U.S. PATENT DOCUMENTS

| | | | |
|---|---|---|---|
| 3,741,205 | 6/1973 | Markolf et al. | 606/61 |
| 4,573,458 | 3/1986 | Lower | 606/69 |
| 4,655,199 | 4/1987 | Steffee | 606/61 X |
| 4,762,122 | 8/1988 | Slocum | 606/70 |
| 4,800,874 | 1/1989 | David et al. | 606/69 |
| 4,854,304 | 8/1989 | Zielke | 606/61 |
| 4,923,471 | 5/1990 | Morgan | 606/60 X |
| 4,959,065 | 9/1990 | Arnett et al. | 606/71 X |
| 5,015,248 | 5/1991 | Burstein et al. | 606/74 |
| 5,041,113 | 8/1991 | Biedermann et al. | 606/61 |
| 5,108,395 | 4/1992 | Laurain | 606/71 X |
| 5,147,361 | 9/1992 | Ojima et al. | 606/61 |
| 5,180,381 | 1/1993 | Aust et al. | 606/61 |
| 5,201,737 | 4/1993 | Leibinger et al. | 606/70 X |
| 5,234,431 | 8/1993 | Keller | 606/61 X |
| 5,261,910 | 11/1993 | Warden et al. | 606/61 |
| 5,290,312 | 3/1994 | Kojimoto et al. | 606/61 X |
| 5,318,567 | 6/1994 | Vichard | 606/71 X |
| 5,324,290 | 6/1994 | Zdeblick et al. | 606/61 |

FOREIGN PATENT DOCUMENTS

| | | | |
|---|---|---|---|
| 2254304 | 7/1975 | France | 606/61 |
| 1049056 | 10/1983 | U.S.S.R. | 606/71 |
| 1175464 | 8/1985 | U.S.S.R. | 606/61 |
| 2011819 | 7/1992 | WIPO | 606/61 |

OTHER PUBLICATIONS

McBride S.M.O. Stainless Steel Bone Plates, 1943, De Puy. Operative Surgery, vol II, Brickham, Pub. Saunders London, 1924.
Vitallium Surgical Appliances Catalog, p. 7, 3–1948.

*Primary Examiner*—Robert A. Hafer
*Assistant Examiner*—Brian E. Hanlon
*Attorney, Agent, or Firm*—Tarolli, Sundheim, Covell, Tummino & Szabo

[57] ABSTRACT

An anterior spinal fixation device which provides an anterior lumbar and cervical fusion fixation system which has numerous advantages over existing anterior, posterior and lateral implant systems. Anterior (access from the patient's stomach region) lumbar surgery allows the surgeon to remove the entire intervertebral disc, which is not possible during posterior or lateral surgery. Many interbody fusion operations require removal of disc material, insertion of new graft material and fusion of the adjoining vertebrae. This pate and screw fixation invention provides the ability to perform this function. The novelty of this invention includes overall design allowing for multiple fusions, a bicortical fixation system which is achieved by inserting four screws at a 45 degree angle into two cortical surfaces. It also provides structural integrity by placing more friction on the screws which allows for increased pull out strength. An anterior fixation device also is further from the spinal cord which reduces the chance of contact with the new roots.

5 Claims, 2 Drawing Sheets

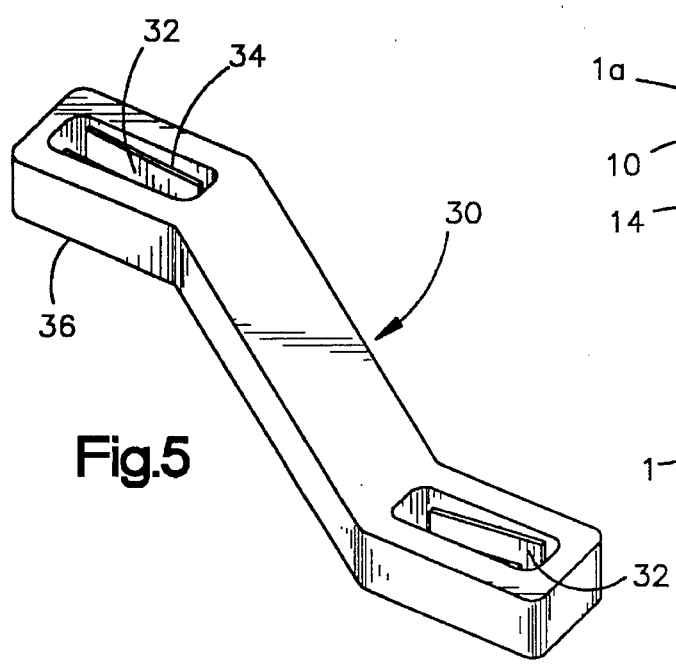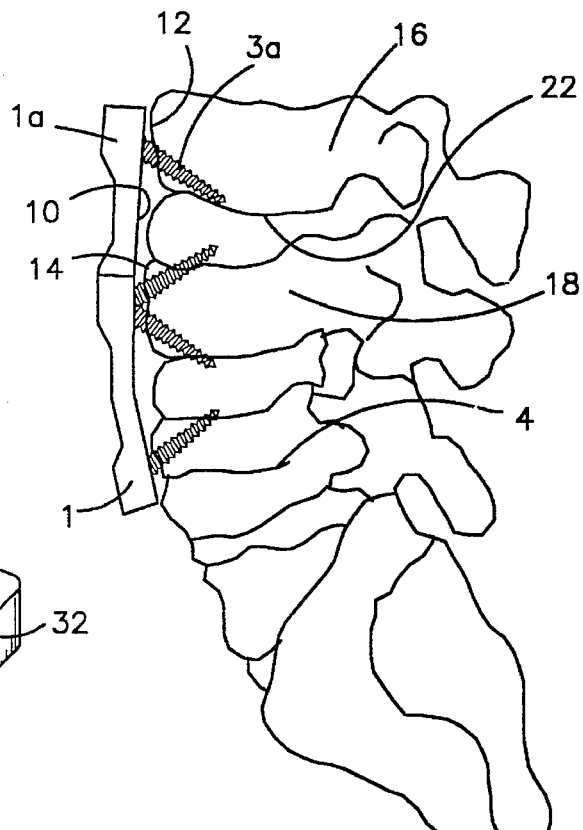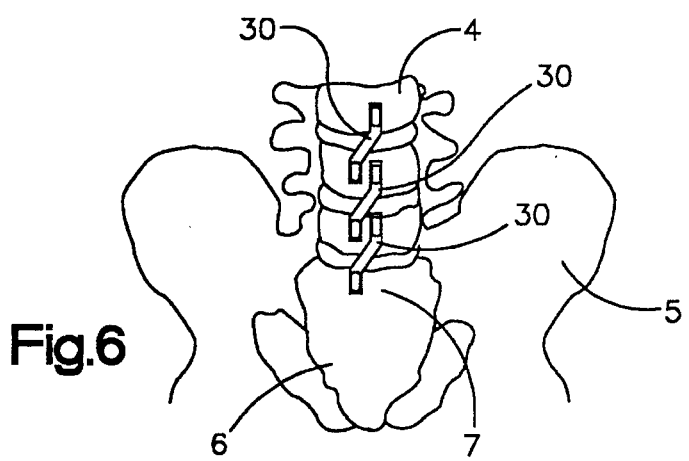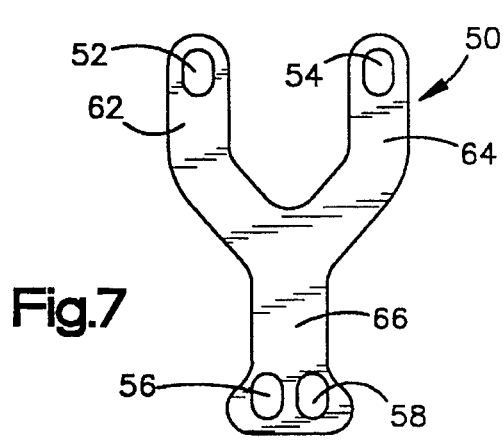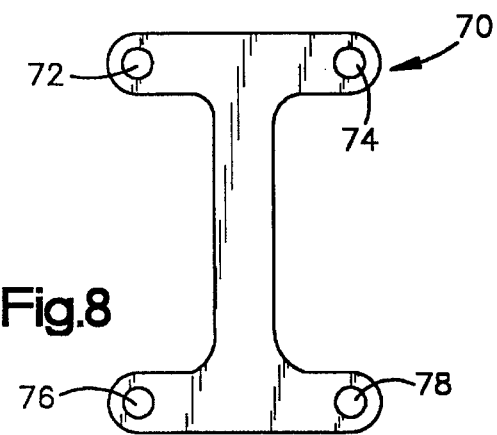

ANTERIOR LUMBAR/CERVICAL BICORTICAL COMPRESSION PLATE

This is a continuation of application(s) Ser. No. 07/987, 140 filed on Dec. 8, 1992 now abandoned which is a continuation-in-part of Ser. No. 07/765,014, filed on Sep. 24, 1991, now U.S. Pat. No. 5,180,381.

BACKGROUND OF THE INVENTION

This invention relates to an interbody fusion system that is installed on a portion of the spine and serves to mechanically fuse vertebral bodies.

The evolution of daily physical demands on the human body have continued to decrease in the workplace due to great advances in industrial automation. Most jobs today involve sitting for long periods of time. During relaxed sitting, the loads on the lumbar spine are greater than during upright standing. Thus, our "sitting" work style and active sports during our leisure time have significantly increased the amount of spinal problems. Loads on the spine are produced primarily by body weight, muscle activity, and externally applied loads. Since the lumbar region is the main load bearing area of the spine, and the area where pain most commonly occurs, lumbar, as well as cervical spinal surgery has become a demanding and growing field of surgery. Also, as a result of aging, and a more recreationally active population, the number of spinal fusions performed in the U.S. has grown significantly.

The objective of spinal implants is to facilitate fusion of elements of the spine. This invention addresses this issue.

The percentage of spinal fusions (using spinal implants) has increased over the past few years but is still less than 50%. Most spinal fusions are actually candidates for spinal implants.

The spinal implant market has been the most rapidly growing segment of the orthopedic market in recent years.

The primary factors responsible for the strong growth in the use of spinal implants are innovations in the design of spinal implant devices, changing physician attitudes toward the use of such devices, and the growing number of orthopedic surgeons trained in the use of such implants.

Spinal fusions are performed to treat degenerative diseases, deformities, and trauma, but until recently, surgeons had limited implant options for treating spinal conditions. Physicians treating spinal conditions either did so without implants, or utilized basic implant devices. These devices did not, however, provide the patient with sufficient structural stability, and the fusion system and efficacy were limited.

In seeing better alternatives for spinal fusions, physicians began to use plates and screws designed primarily for use on bones in other areas of the body. Due to the perceived risk of paralysis, spinal implants were slow to become popular among physicians. Now various plate, rod and screw implants have been specifically designed for the spinal region and the efficacy of these implants have been proven. Clinical studies have shown that surgeries using spinal implants are more effective at providing structure and rigidity to the spine than surgeries in which implants are not used.

This invention is a continuation in this area of development and provides for the first time an anterior lumbar and cervical fusion fixation system which has numerous advantages over posterior and lateral spinal implant systems.

Anterior (access from the patient's stomach region) lumbar and cervical surgery allows the surgeon to remove the entire intervertebral disc, which is not possible during posterior or lateral surgery. Spinal fusion operations require removal of disk material, insertion of new graft material and mechanical fusion of the adjoining vertebrae.

Surgical operations performed to date do not allow the surgeon the means to keep the graft material in place nor does it allow the surgeon the ability of evenly distributing the loads on the graft material. The proposed anterior fusion procedure with an anterior plate captures both of these tasks.

Posterior and lateral fusion and fixation operations do not allow the surgeon total access to the vertebral inner disc and does not provide a fixation device that eliminates all bending moments.

Not having direct access to the intervertebral disk, the surgeon is unable to extract the entire disk which when inserting the graft material creates additional problems and may not remedy the problem disc. Posterior and lateral spinal operations involve working closer to the spinal cord than do anterior operations. The extra clearance gained by anterior surgery significantly reduces the chance of disrupting the spinal cord and electrical impulses.

This invention allows the surgeon full access to the vertebral intervertebral disc and once installed, the fixation device is installed closer to the center of rotational moment which significantly reduces the bending moment loads on the spine.

One object of the invention is to provide an anterior fusion mechanical fixation device that allows the surgeon full access to the intervertebral disc.

Another object of the invention is the provision of a fixation device that eliminates the need for post operative body jackets.

Yet another object of the invention is the provision for a mechanical fixation device that provides a restraint for the implanted graft material so the chance for displacement of the disc graft material is significantly reduced.

Yet another object of this invention is to provide a better mechanical stabilization method that is biomechanically sound and eliminates bending moments in the vertebral bodies.

Another object of this invention is to provide an improved method and apparatus to maintain vertebrae in a desired spatial relationship and wherein a fastener extends through transverse side surface areas on one of the vertebrae.

Another object of this invention is to provide an improved method and apparatus to maintain vertebrae in a desired spatial relationship and wherein a fastener contacts two cortical surface of a vertebra.

The novelty and key to this system is its bicortical fixation systems which allows the surgeon to install a screw into two cortical bone surfaces. No other system employs such a design and for the first time creates a significantly increased pullout strength and safety factor. Mechanical advantages include increased screw friction which reduces the risk of screw pull out, moment arm stress reduction due to closeness of fixation system to center line of rotation, ability to use smaller fixation screw hardware thus allowing smaller holes in the bone and compression device which pull the two vertebral bodies together to insure bone grafting stabilization.

SUMMARY OF THE INVENTION

In accordance with our invention, we overcome the above difficulties by providing an anterior lumbar and cervical fixation device that allows the surgeon full access to the disk area, a fixation system that captures two cortical surfaces via screw insertion, a fixation system that pulls the two vertebral bodies closer together insuring a tight fusion, a fixation point closer to the center of rotation to reduce torsional loads and provides a physical barrier to reduce the change of displacement of the graft material.

The materials used to provide the basis design are FDA approved human implant metals such as 316L stainless steel, titanium, titanium-vanadium-aluminum and chromium-molybdenum.

The surgical process involves removing the patient's existing intervertebral disc, inserting the bone graft material to replace the extracted disc, pre-drilling screw holes penetrating both cortices of the vertebra, and installing the plate.

Although it is preferred to install the fixation device on lumbar and cervical vertebra, it will be apparent to persons having experience with the mechanical fusing of vertebrae bodies that the fixation device could be installed on thoracic vertebrae if desired. While the fixation device is described in conjunction with anterior portions of the vertebrae, the device could also be used in conjunction with posterior portions of the vertebra.

BRIEF DESCRIPTION OF THE DRAWINGS

A typical fixation device embodying features of our invention is illustrated in the accompanying drawings form part of this application in which:

FIG. 4 is an enlargement of FIG. 2;

FIG. 5 is a perspective view of a second embodiment of the fixation device;

FIG. 6 is a front (anterior) view showing three of the fixation devices of FIG. 5 installed;

FIG. 7 is a plan view of a third embodiment of the fixation device; and

FIG. 8 is a plan view of a fourth embodiment of the fixation device.

DETAILED DESCRIPTION

Figure 1:
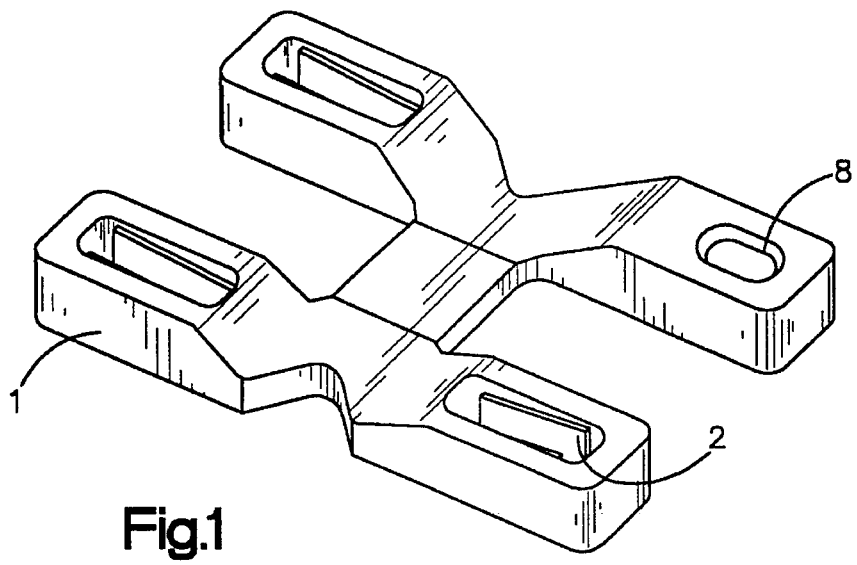
FIG. 1 is a perspective view showing the typical fixation device.

As shown in the drawings, the preferred lumbar fixation device in accordance with the present invention includes a fixation plate 1 which is comprised of FDA approved metal implant material. Overall dimensions of plate 1 are 27 mm in width, 52 mm in length and 1–5 mm thick. As shown in FIG. 1, one preferred embodiment of the fixation plate 1 has four arms or limbs extending from a center portion. There are four slotted screw holes or four countersunk holes for installing the plate onto the spine. As shown in FIG. 1, each hole extends through a respective arm. These stainless steel cortical or cancellous screws have round hex heads and rest on a sloping compression shelf 2 or countersunk hole 8 which distributes the loads to both cortical bone surfaces in the required manner.

Figure 2:
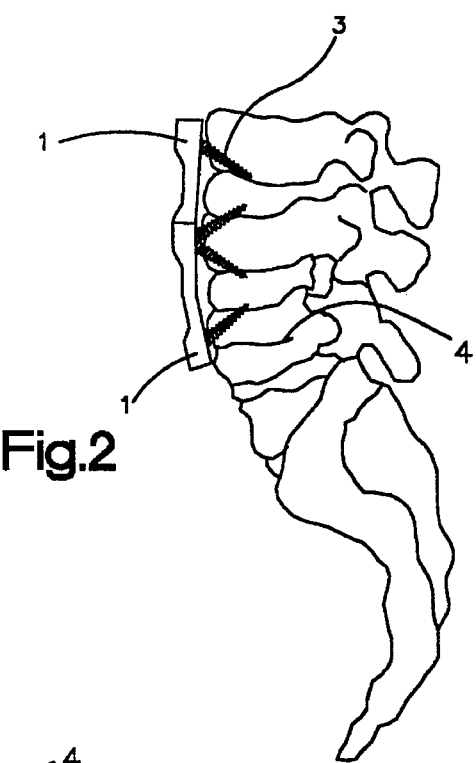
FIG. 2 is a side view of the lower spine (lumbar) region with two fixation devices installed with cortical screws on lumbars-L4 and L5.
Figure 3:
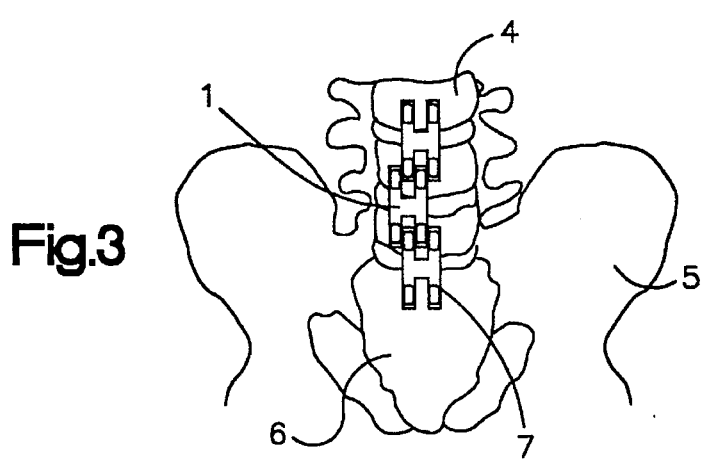
FIG. 3 is a front (anterior) view of the lumbar/pelvic area showing three fixation devices installed on L3, L4, L5 and S1. Plate 7 is different than the other lumbar plates due to the angle and configuration of the sacrum.

FIG. 2 depicts a side view of the lower spine which includes the vertebral bodies and the sacrum and showing the aforementioned screws 3 in place along with two fixation plates 1. The four screws 3 are installed at approximately a 45 degree angle to contact two cortical surfaces of the vertebral body. The fixation plates 1 and screws 3 are installed from and on the anterior side of the spinal region (lumbar or cervical) for the purpose of fusing two or more vertebrae. FIG. 3 shows a front (anterior) view of the lumbar/pelvic region 4, 5, 6 with three fixation plates 1 installed on vertebral bodies L3, L4 and L5. Fixation plate 7 is shown installed on the L5-S1 interface. If desired the fixation plates 1 could be installed at other locations along the spinal column.

As perhaps may be most clearly seen in FIG. 4, which is an enlargement of FIG. 2, the fixation plates are used to maintain vertebra in a desired spatial relationship. The vertebra has an anterior cortical side surface area 12 and a facet cortical side surface area 22. Thus, a fixation plate 1 has a side surface 10 which engages side surface areas 12 and 14 on a pair of adjacent vertebrae 16 and 18. A plurality of openings have been drilled through the vertebra. The opening in the vertebra 16 extend from the side surface area 12 to a side surface area 22 which extends transversely to side surface area 12.

A threaded screw fastener 3a extends through the opening in the vertebra 16 and through an opening in the plate 1a. Thus, a head end portion of the fastener 3a is disposed adjacent to a left (as viewed in FIG. 4) side of the plate 1a. A shank portion of the fastener 3a extends through the first side surface area 12, an anterior portion of the vertebra 16, and to a second side surface area 22 on the vertebra 16.

Since the second side surface area 22 on the vertebra 16 extends transversely to the first side surface area 12 on the vertebra 16, the screw 3a penetrates both cortices of the vertebra and thereby resists pullout. This allows a smaller fixation screw 3a to be used. Although the plate 1a is advantageously installed on the anteriorly facing side of the spinal column, it is contemplated that the plate 1a could be installed on the posteriorly facing side of the spinal column if desired.

A second embodiment of the fixation plate is illustrated in FIG. 5. Thus, a fixation plate 30 (FIG. 5) has a generally S-shaped configuration and forms a second embodiment of the fixation plate. The fixation plate 30 is comprised of FDA approved metal implant material. There are two slotted screw holes 32 for installing the fixation plate 30 on the spine. Slots or screw holes 32 have sloping sides 34 which extend at an acute angle to a lower (as viewed in FIG. 5) side 36 of the fixation plate 30.

FIG. 6 is an illustration depicting the manner in which a plurality of fixation plates 30 are installed on an anteriorly facing side of a spinal column. Thus, the fixation plate 30 is installed on a pair of adjacent vertebrae by first drilling openings in the vertebrae. Each of the openings extends through a first or anteriorly facing side of a vertebra and through a second side of the vertebra. The second side of the vertebra extends transversely to the first side of the vertebra.

The plate 30 is positioned in engagement with the first or anteriorly facing side of the vertebra. The screw is then threaded into the opening formed in the vertebra. The screw extends through the plate and through the side surface of the vertebra. The screw also extends through the second side surface of the vertebra.

To provide for engagement of the screw with the two transversely extending sides of the vertebra, the screw is advantageously installed at an angle of approximately 45 degrees. This results in the screw being disposed in contact with two cortical surfaces of the vertebra. If desired, one of the patient's existing intervertebral discs is removed and bone graft is inserted to replace the extracted disc before the plate 30 is installed. Of course, the plate 30 could be installed without removing a disc and inserting bone graft material if desired.

Since various changes and modifications of the invention will occur to those skilled in the art within the spirit of the invention, the invention is not to be taken as limited except by the scope of the appended claims. Depending on the purpose of the fixation device it is reasonable to think that one might want to vary the materials to use other FDA approved metals such as titanium, titanium-vanadium-aluminum or cobalt-chromium-molybdenum as well as change the basic shape.

Although the foregoing description has been in conjunction with installation of the plates 1 and 30 on the anterior side of a spinal column, the plates could be installed on the posterior side of the spinal column if desired. Although the plates 1 and 30 have been illustrated as being installed on lumbar vertebrae, the plates could be installed on cervical and/or thoracic vertebra if desired.

A third embodiment of the fixation plate is illustrated in FIG. 7. Thus, a fixation plate 50 (FIG. 7) has a generally Y-shaped configuration and forms a third embodiment of the fixation plate. The fixation plate 50 is comprised of FDA approved metal implant material. There are four slotted screw holes 52, 54, 56 and 58 for installing the fixation plate 50 on the spine. Two of the slotted screw holes 52 and 54 are formed on outer end portions of arms 62 and 64 of the Y-shaped fixation plate. In addition, two slotted screw holes 56 and 58 are formed in a lower (as viewed in FIG. 7) end portion of a main section 66 of the fixation plate 50.

A plurality of fixation plates 50 may be installed on an anteriorly facing side of a spinal column. Thus, the fixation plate 50 is installed on a pair of adjacent vertebrae by first drilling openings in the vertebrae. Each of the openings extends through a first or anteriorly facing side of a vertebra and a second side of the vertebra. The second side of the vertebra extends transversely to the first side of the vertebra.

The fixation plate 50 is positioned in engagement with the first or anteriorly facing side of the vertebra. A plurality of screws are then threaded through the fixation plate 50 into the openings formed in the vertebra. The screws extend through the openings 52, 54, 56 and 58 in the plate 50 and through the side surface of the vertebra. The screws also extend through a second side surface of the vertebra. The fixation plate 50 may be mounted with the main portion 66 of one fixation plate disposed between the arms 62 and 64 of a next lower fixation plate.

A fourth embodiment of the fixation plate is illustrated in FIG. 8. Thus, a fixation plate 70 (FIG. 8) has a generally I-shaped configuration and forms a fourth embodiment of the fixation plate. The fixation plate 70 is comprised of FDA approved metal implant material. There are four screw holes 72, 74, 76 and 78 for installing the fixation plate 70 on the spine. In the illustrated embodiment of the invention, the screw holes 72, 74, 76 and 78 have a circular configuration. However, the screw holes 72–78 could have a configuration similar to the slotted screw holes 32 of the fixation plate 30 (FIG. 5) or the slotted screw holes 2 of the fixation plate 1 (FIG. 1).

The fixation plate 70 is installed on a pair of adjacent vertebrae by first drilling openings in the vertebrae. Each of the openings extends through a first or anteriorly facing side of a vertebra and through a second side of the vertebra. The second side of the vertebra extends transversely to the first side of the vertebra.

The plate 70 is positioned in engagement with the first or anteriorly facing side of the vertebra. Screws are then threaded through the plate 70 into the openings formed in the vertebra. The screws extend through the openings 72, 74, 76 and 78 in the plate 70 into the openings formed in the vertebra. The screws also extend through the second side surface of the vertebra. The fixation plate 70 may be mounted on the vertebrae with the upper end portion of a lower fixation plate disposed above the lower end portion of an upper fixation plate.

What is claimed is:

1. A method of maintaining vertebrae in a desired spatial relationship, including forming an opening extending through a first side surface area on one vertebra and through a second side surface area on the one vertebra, the first side surface area on the one vertebra extending transverse to the second side surface area on the one vertebra, positioning a structural means adjacent the vertebrae, and connecting the structural means to the one vertebra with a threaded fastener including locating the threaded fastener in the opening to extend through the first and second side surface areas on the one vertebra.

2. A method as set forth in claim 1, wherein said step of positioning a structural means adjacent the vertebrae includes positioning the structural means adjacent to anteriorly facing sides of the vertebrae, and said step of connecting the structural means to the one vertebra with a threaded fastener includes locating the threaded fastener to extend through an anteriorly facing side area on the one vertebra and through a side surface area on the one vertebra which extends transverse to the anteriorly facing side surface area.

3. A method as set forth in claim 1, wherein said step of connecting the structural means to the one vertebra with a threaded fastener includes engaging a threaded surface means of the threaded fastener with the first and second side surface areas.

4. A method for maintaining vertebrae in a desired spatial relationship, said method comprising:
   positioning a structural means adjacent a vertebra; and
   installing a threaded fastener to extend through the structural means, through the anterior cortical surface area of the vertebra, through the vertebra, and through the facet cortical surface area of the vertebra, said step of installing a threaded fastener including the step of engaging a threaded surface portion of the threaded fastener with the facet cortical surface area.

5. A method as set forth in claim 4, wherein said step of installing a threaded fastener includes engaging a threaded surface portion of the threaded fastener with the anterior cortical surface area.

\* \* \* \* \*